(12) United States Patent
Shwarz et al.

(10) Patent No.: US 11,965,888 B2
(45) Date of Patent: Apr. 23, 2024

(54) QUANTIFYING ENDOTOXIN LOAD IN BACTERIAL BIOFILMS

(71) Applicant: DePuy Synthes Products, Inc., Raynham, MA (US)

(72) Inventors: Erica Shwarz, Philadelphia, PA (US); Wojciech Czaja, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 376 days.

(21) Appl. No.: 17/223,289

(22) Filed: Apr. 6, 2021

(65) Prior Publication Data

US 2021/0318314 A1    Oct. 14, 2021

Related U.S. Application Data

(60) Provisional application No. 63/007,430, filed on Apr. 9, 2020.

(51) Int. Cl.
*C12Q 1/00* (2006.01)
*C12Q 1/06* (2006.01)
*G01N 33/579* (2006.01)

(52) U.S. Cl.
CPC ............ *G01N 33/579* (2013.01); *C12Q 1/06* (2013.01)

(58) Field of Classification Search
CPC ................................ G01N 33/579; C12Q 1/06
See application file for complete search history.

(56) References Cited

PUBLICATIONS

Chaignon et al. 2007 (Susceptibility of staphylococcal biofilms to enzymatic treatments depends on their chemical composition; Appl . Microbiol. Biotechnol. 75:125-132; 75:125-132). (Year: 2007).*
Schwarz et al. 2017 (Biological activity of Masked Endotoxin; Scientific Reports 7:44750; of record) (Year: 2017).*
West-Barnette et al. 2006 (Biofilm Growth Increases Phosphorylcholine Content and Decreases Potency of Nontypeable Haemophilus influenzae Endotoxins; Infection and Immunity 74(3): 1828-1836) (Year: 2006).*
Rioufol et al. 1999 (Quantitative determination of endotoxins released by bacterial biofilms; Journal of Hospital Infection 43:203-209) (Year: 1999).*
Lahiri et al. 2021 Bacterial Cellulose: Production, Characterization, and Application as Antimicrobial Agent; International Journal of Molecular Sciences 22: 12984 (Year: 2021).*
Harald Schwarz et al., Biological Activity of Masked Endotoxin, Scientific Reports, vol. 7, No. 1, Mar. 20, 2017, 11 pgs. XP055619479.
Rioufol et al., Quantitative Determination of Endotoxins Released by Bacterial Biofilms, Journal of Hospital Infection, Elsevier, Amsterdam, NL, vol. 43, No. 3, Nov. 1, 1999, pp. 203-209, XP000996287.
Sandle, Endotoxin Testing as a Detection Method for Bacterial Biofilms, American Pharmaceutical Review Endotoxin Supplement, Jan. 1, 2018, pp. 22-25, XP055812778, Retrieved from the Internet: URL:https://www.americanpharmaceuti calrevi ew.com/Featured-Articles/557459-Endotoxin-Testing-as-a-Detection-Method-for-Bacteria 1-Biofilms/ [retrieved on Jun. 10, 2021].
Strap et al, Characterization of Pellicle Inhibition in Gluconacetobacter xylinus 53582 by a Small Molecule, Pellicin, Identified by a Chemical Genetics Screen, PLOS ONE, vol. 6, No. 12, Dec. 9, 2011, p. e28015, XP055816615.
Ruhal et al., Biofilm patterns in gram-positive and gram-negative bacteria, Microbiological Research 251, 2021, 126829, 8 pages.
Wang et al., Impact of biofilm matrix components on interaction of commensal *Escherichia coli* with gastrointestinal cell line HT-29, Cellular and Molecular Life Sciences, 63, 2006, 2352-2363.

* cited by examiner

*Primary Examiner* — Albert M Navarro
(74) *Attorney, Agent, or Firm* — BakerHostetler

(57) ABSTRACT

Disclosed herein are methods for quantifying total endotoxin load in a biofilm sample. Also provided are methods for identifying a gram-negative biofilm derived bacterial infection. The disclosed methods more accurately define actual total endotoxin levels and can detect the presence of endotoxin in a given biofilm volume at a higher resolution than current extraction techniques.

22 Claims, No Drawings

QUANTIFYING ENDOTOXIN LOAD IN BACTERIAL BIOFILMS

CROSS REFERENCE TO RELATED APPLICATION

The present application claims benefit of priority to U.S. Provisional Application No. 63/007,430, filed Apr. 9, 2020, the entire contents of which are hereby incorporated by reference.

FIELD OF DISCLOSURE

The present disclosure is directed to methods of quantifying endotoxins in a biofilm.

BACKGROUND

Currently, a number of medical devices, such as, for example, dura replacement patches, hernia meshes, and wound dressings, are manufactured from bacterial-derived cellulose, which is a form of biofilm. Certain bacteria used to produce the cellulose include gram-negative bacteria. One issue specific to gram-negative bacteria is the presence of endotoxins. Endotoxins, also known as lipopolysaccharides, are part of the bacterial cell wall structure of gram-negative bacteria. They are known pyrogens, and are contributors of inflammatory processes in the body when released from the cell wall, such as during cell division or cell death.

In order to receive regulatory approval, products utilizing or created with gram-negative bacteria must be treated to render them non-pyrogenic.

The FDA-approved standard for bacterial endotoxin testing (BET) is the Limulus Amebocyte Lysate (LAL) assay. This test is outlined for medical devices in ANSI/AAMI ST72:2011, USP <85> and USP <161>. This assay involves contacting the sample with amoebocyte lysate from the Atlantic horseshoe crab (*Limulus polyphemus*). There are three variations to this assay, which include the gel-clot technique, the turbidimetric technique, and chromogenic technique. The gel-clot method is the simplest and most widely used LAL test, and relies upon the formation of a gel. The turbidimetric technique relies upon the development of turbidity in the sample after cleavage of an endogenous substrate. The chromogenic technique is based upon the development of color in the sample after cleavage of a synthetic peptide-chromogen complex. In the event of conflicting test results, the gel-clot test is considered the determinant test method.

Presently, BET on medical devices relies upon an indirect extraction method to quantify endotoxin units (EU). A sample is typically immersed in non-pyrogenic water and heated to approximate body temperature (e.g., 37° C.) for at least an hour. An extract from the water is taken and tested with the LAL assay for endotoxin amount. From that indirect measurement, an EU value is determined for the medical device. Depending upon the intended use of the medical device the FDA sets an acceptable threshold EU value.

From a clinical standpoint, currently biofilms are not easy to detect in a patient who has a biofilm derived bacterial infection. In order to identify an antibiotic treatment course, a tissue sample from the patient is typically cultured and then the bacterial growth is identified. This process is time consuming and is only capable of measuring the number of living bacteria cells capable of growing on the chosen agar under the selected incubation conditions. In certain conditions, viable gram-negative bacteria from a biofilm sample are not detected. Where the infection derives from a gram-negative biofilm, the presence of endotoxins can provide an alternative method of identifying the presence of a biofilm infection in a patient.

SUMMARY

The present disclosure is directed to methods of quantifying endotoxins in biofilm. The methods disclosed herein more accurately define the actual total endotoxin levels and can detect the presence of endotoxin in a given biofilm volume at a much lower level than utilizing current extraction techniques. The methods described herein, therefore, are an improvement over current state of the art methods, and can be used additionally, in determining potential biofilm derived infections in a patient suffering from a gram-negative bacterial infection.

According to the present disclosure, methods for quantifying an endotoxin concentration in a biofilm include the steps of:
digesting the biofilm sample with an enzyme to form a digested biofilm sample;
separating the digested biofilm sample into a supernatant and a cell pellet;
combining the cell pellet with a cell lysing agent to release endotoxins and form an endotoxin suspension;
concentrating the endotoxin suspension into an endotoxin sample and a suspension supernatant; and,
performing a bacterial endotoxin test (BET) assay on the endotoxin sample to obtain a sample endotoxin value.

According to certain embodiments, the biofilm is comprised of cellulose;
preferably, the biofilm is comprised substantially of bacterial-derived nanocellulose (BNC). According to the disclosure, the biofilm is comprised of, at least partially, endotoxin producing microbes, for example, gram-negative bacteria. In a preferred embodiment, the gram-negative bacteria is from the genus *Gluconacetobacter*.

In certain embodiments, the digesting step can include a heating step. In certain embodiments, the enzyme utilized in digesting includes a cellulase. In additional embodiments, the cell lysing agent comprises a chelating agent and a salt.

In certain embodiments, the methods can further include the step of diluting the endotoxin sample prior to the step of performing the BET assay. According to further embodiments, the methods can include the step of adding a beta-glucan inhibitor to the endotoxin sample. In additional embodiments, the methods can further include performing a colony forming unit (CFU) assessment of the biofilm sample to obtain a CFU value, such that a relationship between the endotoxin value and the CFU value can be determined.

The present disclosure further discloses methods for clinically identifying a gram-negative biofilm derived bacterial infection. The methods include:
enzymatically digesting a mammalian tissue sample to form a digested tissue sample;
separating the digested tissue sample into a supernatant and a cell pellet;
combining the cell pellet with a cell lysing agent to release a quantity of endotoxins, wherein the quantity of endotoxins has a lower limit of zero;
concentrating the quantity of endotoxins, and,
performing a bacterial endotoxin test (BET) assay on the concentration to obtain a tissue sample endotoxin value.

In certain embodiments, the biofilm is comprised of pathogenic microbes, for example, gram-negative bacteria from the family Enterobacteriaceae.

DETAILED DESCRIPTION

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of the invention, which, for clarity, are described herein in the context of separate embodiments, may also be provided in combination in a single embodiment. Conversely, various features of the invention that are, for brevity, described in the context of a single embodiment, may also be provided separately or in any subcombination.

The present disclosure is directed to methods for quantifying total endotoxin load in a biofilm sample. The methods can include:
  digesting the biofilm sample with an enzyme to form a digested biofilm sample;
  separating the digested biofilm sample into a supernatant and a cell pellet;
  combining the cell pellet with a cell lysing solution to release endotoxins and form an endotoxin suspension;
  concentrating the endotoxin suspension into an endotoxin sample and a suspension supernatant; and,
  performing a bacterial endotoxin test assay on the endotoxin sample to obtain a sample endotoxin value.

According to certain embodiments, the biofilm is comprised of cellulose. With respect to the manufacture of implantable medical devices, in certain embodiments, the biofilm is comprised substantially of bacterial-derived nanocellulose (BNC). According to the disclosure, the biofilm is comprised, at least partially, from endotoxin producing microbes, for example, gram-negative bacteria. In a preferred embodiment, the gram-negative bacteria is a *Gluconacetobacter*. Other gram-negative bacteria known for the production of cellulose can include, for example, *Azotobacter, Rhizobium, Agrobacterium, Pseudomonas, Salmonella*, or *Alcaligenes*.

According to certain embodiments, the biofilm sample is a BNC pellicle. According to certain embodiments, the cellulose content of the sample pellicle can be about 1% to about 50%, for example, about 5%, 10%, 20%, 25%, or 40%.

It should be noted that the materials and equipment utilized in carrying the processes described herein should preferably be depyrogenated prior to use to avoid contamination and potentially cause a false positive result.

The present disclosure describes a step of digesting the biofilm sample with an enzyme to form a digested biofilm sample. This purpose of the digestion step is to break down the extracellular matrix of cellulose entrapping the bacteria contained therein and therefore making the bacteria cell walls more available to the subsequent cell lysing step. While the step of digestion is described in detail below in the context of enzymatic digestion, it should be appreciated that the digestion step could be accomplished chemically, for example, with low concentration of acids. In certain embodiments, the enzyme used is a cellulase enzyme. The amount of enzyme utilized can be determined based upon the amount of biofilm to be digested. A suitable ratio of enzyme to biofilm sample can be about 1:10 to about 1:20. Preferably, the enzyme composition is prepared in a depyrogenated flask or beaker using Highly Purified Water (HPW). The enzyme composition can be vortexed when appropriate. Furthermore, in certain embodiments, the enzyme composition can be filtered prior to use, for example, with a 0.2 μm sterile filter.

According to the present disclosure, the digesting step can further include a heating step. For example, the biofilm sample can be placed in a container with the enzyme composition for digestion and heated, e.g., in a water bath, during the digestion step. A suitable temperature range for digesting the biofilm can be 20° C. to 60° C. A preferred temperature range for digesting cellulose biofilm samples is 45° C. to 55° C. According to certain embodiments, the digestion step can be about 10 hrs to about 48 hrs. A suitable range for the digestion of a cellulose biofilm can be about 10 hrs to about 18 hrs, for example, 15 hrs to 16 hrs. It should be appreciated that digesting can occur with heating during the entire step, or alternatively, heat can be applied for a time period shorter than the length of the digesting step.

After completion of digestion of the biofilm, the methods include a step of separating the digested biofilm sample into a supernatant and a cell pellet. In certain embodiments, the step of separating comprises centrifuging the digested sample. Depending upon the total volume of the digested biofilm sample, the sample can be homogenized (e.g., vortexed) and the sample can be divided into smaller containers for centrifuging. Further, the samples can be centrifuged one or more times to fully concentrate the bacteria cells and form the cell pellet. Where the sample has been separated for centrifuging, the methods necessarily include a step of recombining the sample. According to further embodiments, the methods can also include removing (e.g., aspirating) the supernatant prior to the step of combining the cell pellet with the lysing agent.

After completion of the step of separating the cell pellet, the methods include the step of combining the cell pellet with a cell lysing solution to release endotoxins and form an endotoxin suspension. In certain embodiments, the cell lysing solution is a buffered solution having a pH of 5.5 to 9; preferably of pH 6 to 8. According to certain embodiments, the cell lysing solution comprises a chelating agent. Suitable chelating agents can include EDTA and EGTA, for example. According to certain additional embodiments, the cell lysing solution can include salts, for example, Tris-HCl, Triton X, Tween or Sodium Dodecyl Sulfate (SDS).

According to certain embodiments, the cell pellet can be broken up and the cells homogenously redistributed in the cell lysing solution through, for example, vortexing or other agitation processes. In certain embodiments, the homogenized cells in solution can be heated while the cell lysing process occurs. Suitable temperature ranges for the heating step can be about 20° C. to about 37° C., for example 20° C. to 25° C. Additionally, the homogenized cells in the cell lysing solution can be continuously agitated while the process of cell lysing occurs. For example, a sample can be placed in a heated water bath shaker for anywhere from about 10 min to about 45 min under gentle agitation at a temperature of about 37° C.

Once the step of lysing the cells of the sample is completed, the endotoxins present in the cell walls will have been released forming an endotoxin suspension. The method therefore further includes the step of concentrating the endotoxin suspension into an endotoxin sample and a suspension supernatant. This can be done, according to one embodiment, through the use of centrifuging as previously described above. Additionally, once the endotoxin suspension has been concentrated into an endotoxin sample and supernatant, the supernatant can be removed, e.g., through aspiration, prior to testing the endotoxin sample.

Once an endotoxin sample is obtained, the method includes the step of performing a bacterial endotoxin test (BET) assay on the endotoxin sample to obtain a sample endotoxin value. According to certain embodiments, the BET assay is the Limulus amoebocyte lysate (LAL) assay. The LAL assay is the recognized standard for endotoxin testing by the U.S. Food and Drug Administration (FDA). There are three variations of the LAL assay that are accepted: the gel-clot method, the turbidimetric method, and the chromogenic method.

According to certain embodiments, it is preferable to add a beta-glucan inhibitor prior to performing the BET test. In certain more preferred embodiments, the beta-glucan inhibitor is added immediately prior to the BET test In the LAL test methodology, beta-glucans can interfere with the measurement of endotoxins by giving a false positive. Beta-glucans are present in cellulose, and while the digesting step may eliminate their presence in the subsequent test of the endotoxin sample, there is a possibility that there can still be a not insignificant amount present in the sample to be tested. As such, adding the beta-glucan inhibitor to the sample decreases the possibility of generating false positives in the BET assay. According to certain embodiments, the beta-glucan inhibitor is a commercially available Endotoxin Specific Buffer (ES Buffer).

According to further embodiments, the method can additionally include performing a colony forming unit count of the biofilm sample in order to obtain a CFU value that is used to determine the amount of active bacteria cells in the sample. It is beneficial to the BET analysis to be able to correlate the CFU value of the sample with the endotoxin value of the sample. According to certain embodiments, the method further includes determining the molecular weight of the endotoxin, such that a measured EU value provides a known viable cell count for bacteria in the sample.

The present disclosure further describes methods for identifying gram-negative biofilm-derived infections in a mammal. The ability to quickly identify the type of biofilm-derived infection provides a significant clinical improvement in diagnosing infection and providing the appropriate therapeutic treatment over current methods relying upon culturing for identification of the specific type of pathogenic bacteria causing an infection. With respect to pathogenic bacteria, the biofilm can be comprised at least partially of bacteria from the family Enterobacteriaceae, which can include for example, *Salmonella, Escherichia coli, Klebsiella, Shigella, Enterobacter*, and *Citrobacter*. Other gram-negative microbes are known and within the scope of this disclosure.

According to the disclosure, a method for clinically identifying a gram-negative biofilm derived bacterial infection is described, the method including the steps of:
enzymatically digesting a biofilm sample to form a digested biofilm sample;
separating the digested biofilm sample into a supernatant and a cell pellet;
combining the cell pellet with a cell lysing agent to release a quantity of endotoxins, wherein the quantity of endotoxins has a lower limit of zero;
concentrating the quantity of endotoxins, and,
performing a bacterial endotoxin test (BET) assay on the concentration to obtain a sample endotoxin value.

According to certain embodiments, the biofilm sample is a mammalian tissue sample. In other words, a biopsy of tissue (e.g., blood, bone, muscle) can be taken from a patient suspected of having a biofilm-derived bacterial infections. In certain other embodiments, the source of a suspected biofilm-derived infection may be from an infected implanted medical device in a patient, such as for example, a joint prosthesis, a bone fixation device, a soft tissue device, e.g., hernia mesh, or other implantable medical device well known to those of skill in the art. In such situations, the biofilm sample can be taken from a surface of the suspected infected device. In certain embodiments, the surface biofilm sample is taken from the implanted medical device while the device is still implanted in the patient. In certain other embodiments, the biofilm sample is taken after the device has been removed from the patient.

In embodiments where the sample endotoxin value is greater than zero, the biofilm can be determined to comprise at least partially, pathogenic gram-negative bacteria. According to additional embodiments, determining the endotoxin value can include determining an EU/mL value. As previously explained, CFU to EU correlations can exist such that determining an EU/mL value can provide treating medical personnel information regarding the potency of any determined gram-negative bacterial colony Thus, an additional step can include administering one or more therapeutic agents effective for reducing the presence of pathogenic gram-negative bacteria. This method, therefore provides a clinical benefit of preventing the unnecessary administration of broad-spectrum antibiotics or other types of therapeutic agents that could be administered in the absence of the knowledge that gram-negative pathogens are present in the biofilm, for example, antibiotics otherwise ineffective at treating gram-negative infections.

According to certain embodiments, the molecular weight of the endotoxins of pathogenic gram-negative bacteria can be specific to individual bacterial species, such that the method can further include identifying a pathogenic bacteria from a sample endotoxin value.

EXAMPLES

SYNTHECEL Dura Repair (Depuy Synthes) is an implantable medical device in the form of a nanocellulose biofilm made from *Gluconacetobacter* gram-negative bacteria.

The PTS (Portable Test System) (Charles River) and calibrated test cartridges were used to evaluate each method. The assay had to meet acceptance criteria such as a coefficient of Variation less than 25%, a spike recovery of 50-200%, and onset times which are acceptable to the certificate of compliance provided with the test cartridge.

Further, in certain test runs, traditional cell viability methods were used to estimate the total amount of viable cells at each process point.

Example 1

Preparation of the Cellulase Digestive Enzyme
10 mL of Cellulase enzyme (Cellulase from *Trichodema reesei*, Sigma Aldrich) was diluted in 90 mL of Highly Purified Water (HPW). The mixture was vortexed to ensure homogeneity. Using a 0.2 uM sterile filter, the dilution was filtered into a depyrogenated flask (V=1000 ml). The flask was covered with depyrogenated foil or parafilm until needed for use.

Preparation of the Cell Lysis Solution 0.2 mL of 0.5M EDTA HCl Buffer (pH 8.0) and 1 mL 1M Tris HCL buffer (pH 8.0) were diluted in 100 mL of HPW in a depyrogenated beaker (200 ml). The mixture was vortexed to ensure homogeneity. The beaker was covered with depyrogenated foil or parafilm until needed for use.

Biofilm Sample Preparation

A sample of a harvested cellulose pellicle (*Gluconacetobacter xylinus*) was obtained and the harvested weight was recorded. The pellicle was placed on a depyrogenated steel plate and cut into small pieces of approximately the same size and weight using a depyrogenated scissors.

The sample pellicle pieces were then transferred into the cellulase enzyme flask.

The flask was covered and placed in a water bath shaker set at about 50° C. to initiate cellulose digestion. Digestion time was approximately 12 hours.

Visible observation was done to ensure all pellicle material was digested and no sample pieces could be observed. If necessary, digestion time can be extended until there is no visible presence of the sample pellicle pieces.

The digested sample material was then transferred into sterile centrifuge containers (~500 mL) designated for use with a centrifuge. Sample material is preferably evenly distributed among the centrifuge containers or else blank containers of water are used in order to offset the sample containers. The digestion was centrifuged at 4000 RPM for 15 minutes.

After centrifugation is complete, the supernatant from each centrifuge container was aspirated without disrupting the cell pellet.

Next, 25 mL of HPW was added to each cell pellet, and the cells were homogenously resuspended. The cell mixture from each of the centrifuge containers was combined into one container. If necessary, approximately 5 mL of the 25 mL supply of HPW were reserved to dislodge any cellular material adhering to the sides of the centrifuge containers.

The centrifuge process is optionally repeated 2-3 additional times.

After completion of the final centrifuge, the supernatant from each centrifuge container was aspirated without disrupting the cell pellet.

Next, 50 mL of cell lysis solution was added to the cell pellet and the cells were homogenously resuspended. The cell suspension was placed in a water bath shaker at a temperature of 36-38° C. for about 15 min at a mild agitation setting.

After the cell suspension was removed from the water bath shaker, it was again centrifuged at 4000 PRM for about 15 min. Once completed, the supernatant was aspirated from each centrifuge container ensuring the cell pellet was not disrupted.

Next, 50 mL of HPW was added to each centrifuge container to homogenously resuspend the cells.

Five separate sample were of the cell suspension were taken and diluted in LAL Reagent Water (LRW) at 1:100 dilution factor and vortexed for approximately 1 min.

The sample was then tested with a Charles River Laboratory Portable Test System (PTS) (sensitivity: 1-0.01 EU/mL, 5-0.05 EU/mL) as explained below.

Endotoxin Measurement

Valid test results are determined where the spike recovery is between 50-200%, and the coefficient of variation for reaction times for both the sample and Positive Product Control (PPC) replicate are less than 25%.

After the sample value was acquired, the total sample value in EU was calculated using the following formula:

Calculated sample value=Sample value*first dilution value*second dilution value*third dilution value TABLE 1a Endotoxin Results

| Sample | SPIKE RECOVERY (%) | SAMPLE VALUE (EU/mL) | Calculated Sample Value (EU × $10^6$) |
|---|---|---|---|
| 1 | 82% | 275 | 1.572 |
| 2 | 133% | 1232 | 1.261 |
| 3 | 131% | 525 | 1.055 |
| 4 | 63% | 193 | 3.850 |
| 5 | 109% | 520 | 16.406 |

TABLE 1b

EU and CFU Results

| Sample | SAMPLE VALUE (EU/mL) | Calculated Sample Value (EU × $10^6$) | Calculated Colony Forming Units (CFU × $10^6$) |
|---|---|---|---|
| 1 | 275 | 1.572 | 63.346 |
| 2 | 1232 | 1.261 | 30.438 |
| 3 | 525 | 1.055 | 100.572 |
| 4 | 193 | 3.850 | 18.878 |
| 5 | 520 | 16.406 | 25.922 |

The calculated sample values were compared to the estimated cellular count in the cellulose pellicle prior to processing. The values were comparable in terms of magnitude.

Example 2—Extraction Method

A sample cellulose pellicle was grown with a surface area of approximately 9 inches by 12 inches. The pellicle was cut into approximately equal pieces and placed in LAL Reagent Water (LRW) for one hour at 37° C. An extraction was taken from the LRW and tested using the LAL assay. The recorded EU values are shown below

TABLE 2

| Sample | Sample Value (EU/mL) | Calculated Value (EU/Device) |
|---|---|---|
| 1 | <5.00 * | 200 |
| 2 | 0.45 | 18 |
| 3 | 1.57 | 62.8 |
| 4 | 1.7 | 68 |
| 5 | 5.55 | 222 |
| 6 | 2.69 | 107.6 |
| 7 | 0.96 | 38.4 |
| 8 | 0.588 | 23.52 |
| 9 | 0.4 | 16 |
| 10 | 0.45 | 18 |
| 11 | 0.45 | 18 |
| 12 | 0.88 | 35.2 |

TABLE 2-continued

| Sample | Sample Value (EU/mL) | Calculated Value (EU/Device) |
|---|---|---|
| 13 | 0.044 | 1.76 |
| 14 | 0.08 | 3.2 |

\* the limit of detection for this cartridge was 5.0 EU/mL. The sample did not register a value, so this is the reported sample value Example 3: Extraction vs Digestion/Lysing The following test compared two samples taken from pellicles grown under identical conditions. One sample was prepared and tested according to the prior art extraction method. The sample was immersed in LAL Reagent Water (LRW) for one hour at 37° C. The extraction was sampled and diluted in a 1:100 dilution. The other sample was prepared according to the method described in Example 1.

TABLE 3

| SAMPLE | EU VALUE |
|---|---|
| Extraction method (prior art) | <0.5000 * |
| Example 1 sample | 33.744 |

\* The limit of detection of this cartridge is 0.005 EU/mL At the 1:100 dilution, the lowest result the system can detect is 0.500 Eu/mL. Since the assay did not detect trace endotoxin, the lowest endotoxin value it could report is 0.500 Eu/mL When the biofilm underwent full enzymatic digestion, with the addition of cell lysis techniques, the assay was able to detect significantly more lipopolysaccharides in the sample. For example, in this particular comparative example, the Example 1 method achieved a greater than 65× more sensitivity than the prior art extraction method. According to certain embodiments, the present method can have an increase in sensitivity at least 25%, 30%, 35%, 40%, 50%, or up to about 100% as compared to the extraction method.

What is claimed:

1. A method for quantifying endotoxin concentration in a biofilm sample comprising cellulose from a gram negative bacteria comprising:
   digesting the gram negative biofilm sample with an enzyme for the digestion of extracellular matrix of the gram negative bacteria, wherein the enzyme comprises cellulose, to form a digested biofilm sample;
   separating the digested biofilm sample into a supernatant and a cell pellet;
   combining the cell pellet with a cell lysing agent to release endotoxins and form an endotoxin suspension;
   concentrating the endotoxin suspension into an endotoxin sample and a suspension supernatant; and,
   performing a bacterial endotoxin test (BET) assay on the endotoxin sample to obtain a sample endotoxin value.

2. The method of claim 1, wherein the digesting step further comprises a heating step.

3. The method of claim 2, wherein the heating step occurs at a temperature of about 48° C. to 52° C.

4. The method of claim 1, wherein the step of digesting occurs over a time period of about 12 hrs to about 24 hrs.

5. The method of claim 1, wherein the step of separating comprises centrifuging the digested biofilm sample.

6. The method of claim 1, wherein the cell lysing agent comprises a chelating agent and a salt.

7. The method of claim 6, wherein the chelating agent comprises EDTA-HCl.

8. The method of claim 6, wherein the salt comprises Tris-HCl.

9. The method of claim 1, wherein the step of combining the cell pellet with the cell lysing agent includes suspending cells from the cell pellet in the cell lysing agent.

10. The method of claim 9, wherein the step of suspending cells includes heating to a temperature of about 22° C. to about 26° C.

11. The method of claim 9, further comprising agitating for a time period of about 10 min to about 30 min.

12. The method of claim 1, wherein the step of concentrating the endotoxin suspension comprises centrifuging the endotoxin suspension.

13. The method of claim 1, further comprising the step of diluting the endotoxin sample prior to the step of performing the BET assay.

14. The method of claim 1, wherein the BET assay is the Limulus amoebocyte lysate (LAL) assay.

15. The method of claim 14, wherein the LAL assay is the gel-clot assay.

16. The method of claim 14, wherein the LAL assay is the turbidimetric assay.

17. The method of claim 14, wherein the LAL assay is the chromogenic assay.

18. The method of claim 1, further comprising the step of adding a beta-glucan inhibitor to the endotoxin sample.

19. The method of claim 1, further comprising performing a colony forming unit (CFU) assessment of the biofilm sample to obtain a CFU value, such that a relationship between the endotoxin value and the CFU value is determined.

20. A method of identifying an infection from pathogenic gram-negative bacteria within a gram-negative bacterial biofilm comprising cellulose comprising:
   enzymatically digesting a sample of the gram negative biofilm to form a digested biofilm sample using an enzyme comprising cellulase for the digestion of extracellular matrix of the pathogenic gram negative bacteria;
   separating the digested biofilm sample into a supernatant and a cell pellet;
   combining the cell pellet with a cell lysing agent to release a quantity of endotoxins, wherein the quantity of endotoxins has a lower limit of zero;
   concentrating the quantity of endotoxins, and,
   performing a bacterial endotoxin test (BET) assay on the concentration to obtain a sample endotoxin value, wherein a sample endotoxin value that is greater than zero is indicative of the presence of the pathogenic gram-negative bacteria in the biofilm.

21. The method of claim 20, wherein the biofilm sample is obtained from a mammalian tissue sample.

22. The method of claim 20, wherein the biofilm sample is removed from an implantable medical device surface.

* * * * *

UNITED STATES PATENT AND TRADEMARK OFFICE
CERTIFICATE OF CORRECTION

PATENT NO. : 11,965,888 B2
APPLICATION NO. : 17/223289
DATED : April 23, 2024
INVENTOR(S) : Erica Shwarz et al.

Page 1 of 1

It is certified that error appears in the above-identified patent and that said Letters Patent is hereby corrected as shown below:

In the Claims

Claim 1, Column 9, Line 45, replace "cellulose" with --cellulase--.

Signed and Sealed this
Nineteenth Day of August, 2025

Coke Morgan Stewart
*Acting Director of the United States Patent and Trademark Office*